US009994909B2

(12) United States Patent
Morrison et al.

(10) Patent No.: US 9,994,909 B2
(45) Date of Patent: *Jun. 12, 2018

(54) DIAGNOSTIC METHODS FOR DETERMINING PROGNOSIS OF NON-SMALL CELL LUNG CANCER (71) Applicant: Abbott Molecular Inc., Des Plaines, IL (US)

(72) Inventors: Larry E. Morrison, Lombard, IL (US); John Coon, Oak Park, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 31 days.

This patent is subject to a terminal disclaimer.

(21) Appl. No.: 14/584,788

(22) Filed: Dec. 29, 2014

(65) Prior Publication Data

US 2015/0167102 A1  Jun. 18, 2015

Related U.S. Application Data (63) Continuation of application No. 12/082,709, filed on Apr. 14, 2008, now Pat. No. 8,951,725.

(51) Int. Cl.
*C12Q 1/68* (2018.01)
*C12P 19/34* (2006.01)
*C12M 1/34* (2006.01)
*C07H 21/02* (2006.01)
*C07H 21/04* (2006.01)

(52) U.S. Cl.
CPC ......... *C12Q 1/6886* (2013.01); *C12Q 1/6841* (2013.01); *C12Q 2600/118* (2013.01)

(58) Field of Classification Search
CPC ............... C12Q 1/6841; C12Q 1/6886; C12Q 2600/118
See application file for complete search history.

(56) References Cited

U.S. PATENT DOCUMENTS 8,951,725 B2 * 2/2015 Morrison .............. C12Q 1/6886 435/287.1
2007/0178503 A1 * 8/2007 Jiang .................... C12Q 1/6837 435/6.16

OTHER PUBLICATIONS

Bubendorf L., et al., "Multitarget FISH Analysis in the Diagnosis of Lung Cancer," American Journal of Clinical Pathology, 2005, vol. 123 (4), pp. 516-523.
Carlson J.A., et al., "Chromosome 17 Aneusomy Detected by Fluorescence in Situ Hybridization in Vulvar Squamous Cell Carcinomas and Synchronous Vulvar Skin," American Journal of Pathology, 2000, vol. 157 (3), pp. 973-983.
Choi C.M., et al., "Chromosomal Instability is a Risk Factor for Poor Prognosis of Adenocarcinoma of the Lung: Fluorescence in Situ Hybridization Analysis of Paraffin-Embedded Tissue from Korean Patients," Lung Cancer, 2009, vol. 64 (1), pp. 66-70.
International Preliminary Report on Patentability and Written Opinion for Application No. PCT/US2009/040294, dated Oct. 19, 2010, 6 pages.
International Search Report for Application No. PCT/US2009/040294, dated Jul. 6, 2009, 2 pages.
Kang J.U., et al., "Gain at Chromosomal Region 5p15.33, Containing TERT, Is the Most Frequent Genetic Event in Early Stages of Non-Small Cell Lung Cancer," Cancer Genetics and Cytogenetics, 2008, vol. 182 (1), pp. 1-11.
Kang J.U., et al., "High Frequency of Genetic Alterations in Non-Small Cell Lung Cancer Detected by Multi-Target Fluorescence in Situ Hybridization," Journal of Korean Medical Science, 2007, Suppl. 22, pp. S47-S51.

(Continued)

*Primary Examiner* — Stephen T Kapushoc
(74) *Attorney, Agent, or Firm* — Melissa E. Kolom; Casimir Jones, S.C.

(57) ABSTRACT

The invention provides methods for identifying early stage non-small cell lung cancer (NSCLC) patients who will have a favorable prognosis for the recurrence of lung cancer after surgical resection. The invention is based on the discovery that assessment of chromosomal copy number abnormalities at two or more of chromosome 5p15, 7p12, 8q24 and centromere 6 can be used for prognostic classification. The invention preferably uses fluorescence in situ hybridization with fluorescently labeled nucleic acid probes to hybridize to patient samples to quantify the chromosomal copy number of the these genetic loci. Assessment of the copy number abnormality patterns using four classifiers produced statistically significant prognostic classification for NSCLC: (i) the Range3 pattern of cells showing a difference on a cell by cell basis, of at least three FISH probe signals between the FISH signals at the chromosomal locus with the largest number of FISH signals minus the FISH signals at the chromosomal locus with the lowest number of FISH signals; (ii) the MYC/EGFR % loss pattern assessing the percentage of cells showing fewer MYC FISH probe signals than EGFR FISH probe signals; (iii) a combination of the Range3 pattern and the MYC/CEP6 ratio pattern of a percentage of cells showing a relative loss of MYC FISH probe signals to the FISH probe signal for CEP6; (iv) the combination of the MYC/5p15 ratio pattern showing the relative ratio of MYC and 5p15 locus signals of ≥0.80 and the 5p15/CEP6 ratio pattern assessing percentage of cells having a relative ratio of 5p15 FISH probe signals to CEP6 FISH probe signals ≥1.1 versus MYC/5p15 ratio of <0.80 or 5p15/CEP6<1.1; and (v) a combination of the average range of probe signal differences of equal to or greater than about 2.5 with the Range3 pattern in a percentage of the cells. The invention can be used to identify those early stage NSCLC patients at higher risk of recurrence who should be treated with neo-adjuvant chemotherapy before surgery or with adjuvant chemotherapy after surgery.

6 Claims, 6 Drawing Sheets (56) References Cited

OTHER PUBLICATIONS

Romeo R.S., et al., "Chromosomal Abnormalities in Non-small Cell Lung Carcinomas and in Bronchial Epithelia of High-Risk Smokers Detected by Multi-Target Interphase Fluorescence in Situ Hybridization," Journal of Molecular Diagnostics, 2003, vol. 5 (2), pp. 103-112.

Thisted R.A. What is a P-value?. [retrieved on May 25, 1998] Retrieved from the Internet< URL: http://www.stat.uchicago.edu/faculty/thisted.shtml>, pp. 1-6.

Yang Y., et al., "Parallel Single Cancer Cell Whole Genome Amplification Using Button-Valve Assisted Mixing in Nanoliter Chambers," Plos One, 2014, vol. 9 (9), pp. 1-8.

Zudaire I., et al., "Molecular Characterization of Small Peripheral Lung Tumors Based on the Analysis of Fine Needle Aspirates," Histology and Histopathology, 2008, vol. 23 (1), pp. 33-40.

\* cited by examiner

Figure 2. Time to recurrence grouped by MYC/EGFR%loss, cutoff = 31%

Figure 3. Time to recurrence grouped by Range3 <45% cells AND MYC/CEP6%loss <13% cells versus other cell percentages Figure 4. Time to recurrence grouped by Range3 <45% cells AND MYC/CEP6%loss <24% cells versus other cell percentages Figure 5. Time to recurrence grouped by MYC/5p15 ≥0.80 AND 5p15/CEP6 ≥1.1 versus other ratios Figure 6. Time to recurrence grouped by Ave Range ≥2.5 AND Range3 <42% cells versus other values

DIAGNOSTIC METHODS FOR DETERMINING PROGNOSIS OF NON-SMALL CELL LUNG CANCER

CROSS-REFERENCE TO RELATED APPLICATIONS

This is a continuation of U.S. patent application Ser. No. 12/082,709, filed on Apr. 14, 2008, the entire contents of which are fully incorporated herein by reference.

FIELD OF THE INVENTION

The invention relates to an in vitro diagnostic assay of tissue samples from lung cancer patients for determining patient prognosis, and in particular relates to an in vitro assay for determining prognosis of early stage patients, such as those diagnosed with Stage 1b or Stage II non-small cell lung cancer.

BACKGROUND OF THE INVENTION

Lung cancer accounted for almost one third of cancer deaths in the United States in 2005, and is broadly classified into two types: non-small cell lung cancer and small cell lung cancer. Non-small cell lung cancer (NSCLC) comprises 80-85% of lung cancer cases in the United States. The types of NSCLC are named for the kinds of cells found in the cancer and how the cells look under a microscope. NSCLC comprises three major types: (i) Squamous cell carcinoma, which begins in squamous cells, that are thin, flat cells that look like fish scales. Squamous cell carcinoma is also called epidermoid carcinoma; (ii) Large cell carcinoma, which begins in several types of large lung cells; (iii) Adenocarcinoma, which begins in the cells that line the alveoli of the lung and make substances such as mucus. Other less common types of NSCLC include pleomorphic carcinoma, carcinoid tumor and unclassified carcinoma.

Diagnosis of NSCLC is done by a pathologist's examination of suspected tissue, such as a biopsy sample. After NSCLC diagnosis, the patient's disease is assigned a prognosis (the chance of recovery) using the patient's overall health and age, the severity of symptoms such as coughing and difficulty in breathing, the particular type of NSCLC, and the staging of the cancer. Staging takes into account the size of the tumor and whether the tumor is present in the lung only or has spread to other places in the body. The particular treatment options for a NSCLC patient are then selected based upon these considerations, and the cancer staging is an important component for treatment selection. Patients with early stage NSCLC can be potentially be cured by surgical resection to remove the tumor, but the current diagnostic modalities are not able to predict which patients will recur after surgery.

Two or more separate tumor nodules are present in the same lobe; or (iii) a malignant pleural effusion is present, which is the existence of fluid containing cancer cells in the space surrounding the lung.

The N category depends on which, if any, of the lymph nodes near the lungs are affected by the cancer. In the N0 category, the cancer has not spread to any lymph node. In the N1 category, the cancer has spread to lymph nodes within the lung or into the hilar lymph nodes (those located around the area where the bronchus enters the lung). In N1 category the affected lymph nodes are only on the same side as the cancerous lung. In the N2 category, the cancer has spread to subcarinal lymph nodes (those which are around the point where the trachea branches into the left and right bronchi) or to lymph nodes in the mediastinum (the space behind the chest bone and in front of the heart). In the N2 category, the affected lymph nodes are on the same side of the cancerous lung. In the N3 category, the cancer has spread to lymph nodes near the collarbone on either side, and/or to the hilar or mediastinal lymph nodes on the side opposite the cancerous lung.

The M category depends on whether the cancer has metastasized and spread to any distant tissues and organs. In the M0 category, there is no distant cancer spread. In the M1 category, the cancer has spread to 1 or more distant sites. Sites which are considered distant include other lobes of the lungs, lymph nodes further than those used to determine the N category of the cancer, and other organs or tissues such as the liver, bones, or brain.

Once the T, N, and M categories have been assigned for the particular NSCLC, this information is combined (stage grouping) to assign an overall stage of 0, I, II, III, or IV (see Table 1). Various combinations of the T and N categories are combined into stages. The stages identify tumor types that have a similar prognosis and are treated in a similar way. As noted in Table 1, a tumor with distant spread (i.e. an M1 category cancer) is considered Stage IV, regardless of tumor size of involvement of lymph nodes. The following Table from the NCCN internet web site shows the combined category and stage classification for NSCLC.

TABLE 1

| Overall Stage | T Category | N Category | M Category |
|---|---|---|---|
| Stage 0 | Tis | N0 | M0 |
| Stage IA | T1 | N0 | M0 |
| Stage IB | T2 | N0 | M0 |
| Stage IIA | T1 | N1 | M0 |
| Stage IIB | T2 | N1 | M0 |
|  | T3 | N0 | M0 |
| Stage IIIA | T1 | N2 | M0 |
|  | T2 | N2 | M0 |
|  | T3 | N1 | M0 |
|  | T3 | N2 | M0 |
| Stage IIIB | Any T | N3 | M0 |
|  | T4 | Any N | M0 |
| Stage IV | Any T | Any N | M1 |

NSCLC patients with lower stage numbers generally have a more favorable prognosis and outlook for survival, and these patients are generally treated by surgical resection of the tumor. However, even for early stage patients, such as those with Stage 1B, Stage IIA or IIB NSCLC, a significant percentage of these patients will recur after surgical resection with more aggressive disease and die. The current clinical diagnostic methods are incapable of identifying early stage NSCLC prognosis with sufficient accuracy to direct more aggressive therapy against those patients more likely to recur. Better in vitro diagnostic methods to identify higher risk, early stage NSCLC patients who should receive neoadjuvant or adjuvant chemotherapy or even forgo surgical resection altogether, are therefore needed.

Molecular in vitro diagnostic assays based on fluorescence in situ hybridization (FISH) using fluorescently labeled DNA hybridization probes to identify chromosomal abnormalities have been disclosed for use in the selection of chemotherapy for NSCLC patients, see PCT/US2005/018879, "Methods for prediction of clinical outcome to epidermal growth factor inhibitors by cancer patients", M. Garcia et al. FISH assays have also been used as an initial diagnostic assay for NSCLC, see U.S. Patent Application 20060063194, "Methods and probes for the detection of cancer", L. Morrison et al., published Mar. 23, 2006 (hereafter referred to as "Morrison '194"), which is incorporated herein by reference in its entirety. The Morrison '194 application describes multiple FISH probe sets useful for screening and diagnosis of NSCLC, and one probe set described in Morrison '194 is commercially available as the LAVysion™ probe set from Abbott Molecular, Inc. (Des Plaines, Ill., U.S.A.) under ASR (Analyte Specific Reagent) labeling for use by clinical laboratories to produce clinical diagnostic assays. Under the U.S. Food and Drug Administration ASR labeling requirements, the ASR labeling must not include any claims as to the medical utility of the ASR. The LAVysion ASR probe set comprises four FISH probes: a chromosome 5p15 locus specific probe labeled with the SpectrumGreen green fluorophore, a chromosome 8q24 locus specific probe labeled with the SpectrumGold yellow fluorophore, a chromosome 6 enumeration probe labeled with the SpectrumAqua blue fluorophore, and a chromosome 7p12 locus specific probe labeled with the SpectrumRed red fluorophore.

Multiple research publications describe research performed using the LAVysion probe set, see e.g., M. Garcia et al., "Multi-target interphase fluorescence in situ hybridization assay increases sensitivity of sputum cytology as a predictor of lung cancer", *Cancer Detection and Prevention*, Vol. 24, Issue 4, 2004: 244-251; K. Halling et al., "A Comparison of Cytology and Fluorescence in Situ Hybridization for the Detection of Lung Cancer in Bronchoscopic Specimens", *Chest*, 2006; 130:694-701; and I. Zudaire et al., "Molecular characterization of small peripheral lung tumors based on the analysis of fine needle aspirates", *Histol. Histophathol.* (2008) 23: 33-40. See also the review article K. Hailing et al., "Fluoresence in situ hybridization in diagnostic cytology", *Hum. Path.* (2007) 38: 1137-11444. None of these previous patent applications or publications on FISH assays for NSCLC have disclosed the use of FISH probes to more accurately identify prognosis for early stage NSCLC, in particular, those classified as Stage IB or Stage II.

SUMMARY OF THE INVENTION

The present invention provides a method of determining prognosis of early stage non-small cell lung cancer in a human, the method comprising: (a) providing a biological sample from the human; (b) contacting the biological sample with a set of chromosomal probes comprising at least two probes selected from a group consisting of a chromosome 5p15 locus specific probe, a chromosome 8q24 locus specific probe, a chromosome 6 enumeration probe, and a chromosome 7p12 locus specific probe under conditions sufficient to enable hybridization of probes to chromosomes in the sample, if any; (c) identifying chromosome copy number abnormalities present at each chromosome locus targeted by the probes; and (d) determining prognosis of early stage non-small cell lung cancer in the subject based upon the chromosomal copy number abnormalities identified in step (c). The invention is based on the discovery that detection of abnormal chromosomal copy number patterns from at least two of these four specific chromosome loci can be used to more accurately identify those early stage NSCLC patients more likely to recur after surgical resection. Applicants have identified five distinct classifications of early stage NSCLC based on copy number abnormality patterns in the patient sample that separate patients into favorable (never recurred or did not recur within three years post surgery) and unfavorable (recurred before one year or between one and three years post surgery) prognosis. Preferably, the biological sample is a lung tumor tissue biopsy or resection and the sample has been classified as an early stage cancer, for example, such as any of Stage IB, Stage IIA or Stage IIB, using the TNM staging system. The invention preferably uses in situ hybridization and, more preferably, fluorescent in situ hybridization (FISH) with fluorescently labeled nucleic acid probes or fluorescently labeled probes comprising nucleic acid analogs to determine the copy number at each of these loci. The invention is particularly beneficial for providing improved prognostic information for early stage NSCLC patients and enables improved therapy selection for those early stage NSCLC patients at higher risk of cancer recurrence.

A FISH assay with the LAVysion ASR probe set was used to evaluate chromosomal copy number abnormalities in paraffin embedded NSCLC tumor biopsy samples as a prognostic tool for early stage NSCLC in a cohort of 60 patients, and all had been treated by surgery without chemotherapy. In this cohort, 16 patients developed recurrent lung cancer within one year of surgery; four developed recurrent lung cancer between one and three years after surgery; 16 developed recurrent lung cancer more than three years after surgery; and 24 never developed recurrent cancer, with a minimum of 34.5 months of follow-up after surgery. Various classifiers were derived from the chromosome copy number abnormalities determined by the LAVysion FISH assay. A range of cutoff values for each classifier were used to categorize patients into two groups, and times to cancer recurrence in the two groups were compared by contingency tables (2-sided Fischer's exact test p-values) and Kaplan Meyer analysis (log rank p-values). Five FISH classifiers were found to associate strongly with prognosis when patients that progressed within 3 years of surgery (unfavorable prognosis) were compared to patients that either did not progress or progressed more than 3 years post surgery (favorable prognosis), or when median times to progression (TTR) times were compared between patient groups distinguished by the classifiers. These classifiers are: (i) Range of cells showing a difference on a cell by cell basis, of at least three FISH probe signals between the FISH signals at the chromosomal locus with the largest number of FISH signals minus the FISH signals at the chromosomal locus with the lowest number of FISH signals (hereafter called Range3); (ii) MYC/EGFR % loss, the percentage of cells showing fewer MYC FISH probe signals than EGFR FISH probe signals; (iii) a combination of the Range3 and a percentage of cells (for example, less than 13%) showing a relative loss of MYC FISH probe signals to the FISH probe signal for CEP6 (MYC/CEP6% loss); (iv) a combination of the overall ratio of MYC FISH probe signals to 5p15 FISH probe signals (the MYC/5p15 ratio, equal to the sum of all MYC probe signals in the cells enumerated, divided by the sum of all 5p15 signals in the cells enumerated) and the overall ratio of 5p15 FISH probe signals to CEP6 FISH probe signals (the 5p15/CEP6 ratio, equal to the sum of all 5p15 probe signals in the cells enumerated, divided by the sum of all CEP6 signals in the cells enumerated); and (v) a combination of the average range of probe signal differences in the cells assessed and the Range3 pattern. Each of these five classifiers provides a statistically significant classification of the patients into favorable and non-favorable prognosis, with p values of $p=0.0035$ (Range3); $p=0.0346$ (MYC/EGFR % loss); $p=0.0008$ (Range3 and MYC/CEP6% loss; $p=0.0026$ (MYC/5p15 and 5p15/CEP 6 ratio); and $p=0.0001$ (average range of probe signal differences and Range3) when optimal thresholds (also referred to as cutoffs) are applied to each parameter. as discussed herein. Median times to progression in the Range3 groups were 121 and 14.5 months, respectively, for groups with higher and lower cell percentages (cutoff=42% cells); p=0.0035. Median times to progression in the MYC/EGFR % loss groups were 113 and 53.3 months, respectively, for groups with higher and lower cell percentages (cutoff=42% cells); p=0.0346. Median times to progression in the Range3 and MYC/CEP6% loss groups were 10.1 and 78.8 months, respectively, for patients with lower percentages for both Range3 (cutoff=45%) and MYC/CEP6% loss (cutoff=13%), relative to the other patients; p<0.0001. Median times to progression in the MYC/5p15 and 5p15/CEP 6 ratio groups were 22.7 and 121 months, respectively, for patients with higher ratios of both MYC/5p15 (cutoff=0.8) and 5p15/CEP6 (cutoff=1.1) relative to the other patients; p=0.0046. Median times to progression in the average range of probe signal differences and Range3 groups were 9.86 and 83.1 months, respectively, for patients having combined high average range (cutoff=2.5) and low Range3 (cutoff=42% cells) relative to the other patients; p<0.0001. The methods of the invention are thus able to provide significantly improved prognostic information for early stage NSCLC.

DETAILED DESCRIPTION OF THE INVENTION

NSCLC Prognosis.

The invention includes methods for determining prognosis of NSCLC patients classified as early stage cancers, in particular those classified as Stage IB, Stage IIA or Stage IIB (Stage IIA and IIB are collectively referred to as Stage II) using the widely used TNM staging system. Alternate NSCLC staging systems based upon other diagnostic classifications can be used to identify the patients whose tissue sample may be assayed by the method of the invention. As used herein, an early stage NSCLC refers to a NSCLC tumor that has not spread to more than one lymph node, nor metastasized to any other organ. Early stage NSCLC patients are almost always treated by surgical resection seeking complete tumor removal, yet a significant risk of recurrence exists for these early stage patients even where the tumor is believed completely resected. Current diagnostic modalities do not allow accurate prediction of which of these early stage cancers are high risk for recurrence and thus should be treated post-resection with adjuvant chemotherapy or before the resection using neoadjuvant chemotherapy. The invention provides prognostic identification of those early stage patients at higher risk by determining chromosomal copy number in the patient sample in at least two of these four copy number assessments: three different chromosomal loci: 5p15, 7p12, and 8q24 and the copy number for chromosome 6. For purposes herein, an early stage NSCLC patient with a favorable prognosis is one that is determined to not have either cancer recurrence or progression of the cancer within three years of surgical resection of the patient's tumor; and an early stage NSCLC patient with an unfavorable prognosis is one that is determined to have either cancer recurrence or progression of the cancer within three years of surgical resection of the patient's tumor.

A FISH assay with the LAVysion ASR probe set was used to evaluate chromosomal copy number abnormalities in paraffin embedded NSCLC tumor biopsy samples as a prognostic tool for early stage NSCLC in a cohort of 60 patients, and all had been treated by surgery without chemotherapy. In this cohort, 16 patients developed recurrent lung cancer within one year of surgery; four developed recurrent lung cancer between one and three years after surgery; 16 developed recurrent lung cancer more than three years after surgery; and 24 never developed recurrent cancer, with a minimum of 34.5 months of follow-up after surgery. Five separate classifiers based on chromosomal copy number abnormality patterns identified using the four probe LAVysion set were found to associate strongly with prognosis when patients that progressed within 3 years of surgery (unfavorable prognosis) were compared to patients that either did not progress or progressed more than 3 years post surgery (favorable prognosis), or when median times to progression (TTR) times were compared between patient groups distinguished by the classifiers.

These five classifiers were used to analyze the hybridization pattern from the four probes in 40 to 120 cells of tissue sample. The classifiers are: (i) the Range3 pattern of cells showing a difference on a cell by cell basis, of at least three FISH probe signals between the FISH signals at the chromosomal locus with the largest number of FISH signals minus the FISH signals at the chromosomal locus with the lowest number of FISH signals; (ii) 8q24/7p12% loss pattern (also referred to herein as MYC/EGFR % loss pattern) assessing the percentage of cells showing fewer 8q24 (MYC) FISH probe signals than 7p12 (EGFR) FISH probe signals; (iii) a combination of the Range3 pattern and the 8q24/centromere 6 ratio pattern (also referred to herein as the MYC/CEP6 ratio pattern) of less than about 13% of cells showing a relative loss of 8q24 (MYC) FISH probe signals to the FISH probe signal for CEP6; (iv) the 8q24/5p15 ratio pattern (also referred to herein as the MYC/5p15 ratio pattern) showing the ratio of 8q24 and 5p15 locus signals of ≥0.80 and the 5p15/centromere 6 ratio (also referred to herein as the 5p15/CEP6 ratio pattern) assessing percentage of cells having a relative ratio of 5p15 FISH probe signals to CEP6 FISH probe signals ≥1.1 versus MYC/5p15 ratio of <0.80 or 5p15/CEP6<1.1; and (v) a combination of the average range of probe signal differences of equal to or greater than about 2.5 (herein the Average Signal Range) with the Range3 pattern in less than about 42% of the cells.

Each of these five classifiers provides a statistically significant classification of the patients into favorable and non-favorable prognosis, with p values of p=0.0035 (Range3); p=0.0346 (MYC/EGFR % loss); p=0.0008 (Range3 and MYC/CEP6% loss; p=0.0026 (MYC/5p15 ratio and 5p15/CEP 6 ratio); and p=0.0001 (Average Signal Range and Range3). Median times to progression in the Range3 groups were 121 and 14.5 months, respectively (p=0.0035). Median times to progression in the MYC/EGFR % loss groups were 113 and 53.3 months, respectively (p=0.0346). Median times to progression in the Range3 and relative MYC/CEP6 ratio groups were 10.1 and 78.8 months, respectively (p<0.0001). Median times to progression in the MYC/5p15 and 5p15/CEP 6 ratio groups were 22.7 and 121 months, respectively (p=0.0046). Median times to progression in the Average Signal Range and Range 3 groups were 9.86 and 83.1 months, respectively (p<0.0001). The method of the invention is thus able to provide significantly improved prognostic information for early stage NSCLC.

The prognostic identification of early stage NSCLC of the invention is done on an appropriate biological sample obtained from the patient by in situ hybridization to establish the presence of and pattern of chromosomal abnormalities in the patient sample. In general, in situ hybridization includes the steps of fixing a biological sample, hybridizing one or more chromosomal probes to target DNA contained within the fixed sample, washing to remove nonspecifically bound probe, and detecting the hybridized probe. The in situ hybridization can also be carried out with the specimen cells from the biological sample in liquid suspension, followed by detection by flow cytometry.

The identification of NSCLC prognosis of the invention can also be used with other prognostic in vitro diagnostic assays, such as evaluating the expression in the patient sample of suitable proteins such as EGFR, pAKt and PTEN. Patients whose samples are found with expression of such proteins in conjunction with an abnormal chromosomal copy number pattern, that is associated with an unfavorable outcome (poor prognosis), may be eligible for more aggressive post-surgery treatment, such as chemotherapy.

Chromosomal Probes.

Suitable probes for use in the in situ hybridization methods utilized with the invention for the detection of abnormal copy number pattern (aneusomy or polysomy) are a combination of a chromosome enumeration probe to chromosome 6 and three chromosome locus specific probes, with each probe labeled to be distinguishable from the others. Chromosome enumeration probes hybridize to a chromosomal region, usually a repeat sequence region, and indicate the presence or absence of the target chromosome 6. As is well known in the art, a chromosome enumeration probe can hybridize to a repetitive sequence, located either near or removed from a centromere, or can hybridize to a unique sequence located at any position on a chromosome. For example, a chromosome enumeration probe can hybridize with repetitive DNA associated with the centromere of a chromosome. Centromeres of primate chromosomes contain a complex family of long tandem repeats of DNA comprised of a monomer repeat length of about 171 base pairs, that are referred to as alpha-satellite DNA. A non-limiting example of a specific chromosome enumeration probe is the SpectrumAqua$^M$ CEP® 6 probe (Abbott Molecular Inc.) for chromosome 6. This probe is included in the LAVysion probe set and described in the Examples.

The probe for enumerating copy number of chromosome 6 is used with locus specific probes for detecting copy number abnormalities at each of chromosome 5p15, 7p12 and 8q24, for example to determine the status of amplification and/or polysomy of these loci. A locus specific probe hybridizes to a specific, non-repetitive locus on a chromosome. It is preferred that the 7p12 probe includes at least a portion of the EGFR gene and that the 8q24 probe includes at least a portion of the C-MYC gene. Preferred locus specific probes are the Vysis LSI D5S721, D5S23 SpectrumGreen probe (5p15.2), the Vysis LSI EGFR SpectrumOrange probe (7p12) and the LSI MYC SpectrumGreen probe (8q24), available commercially from Abbott Molecular Inc.

Probes that hybridize with centromeric DNA are available commercially from Abbott Molecular Inc. (Des Plaines, Ill.) and Molecular Probes, Inc. (Eugene, Oreg.). Alternatively, probes can be made non-commercially using well known techniques. Sources of DNA for use in constructing DNA probes include genomic DNA, cloned DNA sequences such as bacterial artificial chromosomes (SAC), somatic cell hybrids that contain one or a part of a human chromosome along with the normal chromosome complement of the host, and chromosomes purified by flow cytometry or microdissection. The region of interest can be isolated through cloning or by site-specific amplification via the polymerase chain reaction (PCR). See, for example, Nath, et al., Siotechnic Histochem, 1998, 73 (1): 6-22; Wheeless, et al., Cytometry, 1994, 17:319-327; and U.S. Pat. No. 5,491,224. The starting human DNA used to manufacture useful locus specific probes can be obtained by obtaining a nucleic acid sequence for the locus from the Human Genome database, such as that maintained by the University of California Santa Cruz, and then using that sequence to screen in silica a SAC human DNA library, such as that maintained by the Roswell Park Cancer Center or Invitrogen, to identify useful BAC clones. Synthesized oligomeric DNA probes or probes made from nucleic acid analogs, such as peptide nucleic acid (PNA) probes, can also be used.

The size of the chromosomal region detected by the probes used in the invention can vary, for example, from the alpha satellite 171 base pair probe sequence noted above to a large segment of 900,000 bases. Locus-specific probes that are directly labeled are preferably at least 100,000 bases in complexity, and use unlabeled blocking nucleic acid, as disclosed in U.S. Pat. No. 5,756,696, herein incorporated by reference, to avoid non-specific binding of the probe. It is also possible to use unlabeled, synthesized oligomeric nucleic acid or unlabeled nucleic acid analogs, such as a peptide nucleic acid, as the blocking nucleic acid.

The chromosomal probes can contain any detection moiety that facilitates the detection of the probe when hybridized to a chromosome. Effective detection moieties include both direct and indirect labels as described herein. Examples of detectable labels include fluorophores (i.e., organic molecules that fluoresce after absorbing light), radioactive isotopes (e.g., $^{32}P$, and $^{3}H$) and chromophores (e.g., enzymatic markers that produce a visually detectable marker). Fluorophores are preferred and can be directly labeled following covalent attachment to a nucleotide by incorporating the labeled nucleotide into the probe with standard techniques such as nick translation, random priming, and PCR labeling. Alternatively, deoxycytidine nucleotides within the probe can be transaminated with a linker. The fluorophore can then be covalently attached to the transaminated deoxycytidine nucleotides. See, e.g., U.S. Pat. No. 5,491,224 to Bittner, et al., which is incorporated herein by reference. Useful probe labeling techniques are described in Molecular Cytogenetics: Protocols and Applications, Y.-S. Fan, Ed., Chap. 2, "Labeling Fluorescence In Situ Hybridization Probes for Genomic Targets", L. Morrison et. al., p. 21-40, Humana Press, © 2002, incorporated herein by reference.

Examples of fluorophores that can be used in the methods described herein are: 7-amino-4-methylcoumarin-3-acetic acid (AMCA), Texas Red™ (Molecular Probes, Inc., Eugene, Oreg.); 5-(and-6)-carboxy-X-rhodamine, lissamine rhodamine B, 5-(and-6)-carboxyfluorescein; fluorescein-5-isothiocyanate (FITC); 7-diethylaminocoumarin-3-carboxylic acid, tetramethylrhodamine-5-(and-6)-isothiocyanate; 5-(and-6)-carboxytetramethylrhodamine; 7-hydroxycoumarin-3-carboxylic acid; 6-[fluorescein 5-(and-6)-carboxamido]hexanoic acid; N-(4,4-difluoro-5,7-dimethyl-4-bora-3a, 4a diaza-3-indacenepropionic acid; eosin-5-isothiocyanate; erythrosine-5-isothiocyanate; 5-(and-6)-carboxyrhodamine 6G; and Cascade™ blue acetyl azide (Molecular Probes, Inc., Eugene, Oreg.). In the LAVysion probe set, fluorophores of different colors are used such that each chromosomal probe in the set can be distinctly visualized.

After hybridization, the probes can be viewed with a fluorescence microscope and an appropriate filter for each fluorophore, or by using dual or triple band-pass filter sets to observe multiple fluorophores. See, e.g., U.S. Pat. No. 5,776,688 to Bittner, et al., which is incorporated herein by reference. Any suitable microscopic imaging method can be used to visualize the hybridized probes, including automated digital imaging systems, such as those available from Meta-Systems or Applied Imaging. Alternatively, techniques such as flow cytometry can be used to examine the hybridization pattern of the chromosomal probes.

Probes can also be labeled indirectly, e.g., with biotin or digoxygenin by means well known in the art. However, secondary detection molecules or further processing are then required to visualize the labeled probes. For example, a probe labeled with biotin can be detected by avidin conjugated to a detectable marker, e.g., a fluorophore. Additionally, avidin can be conjugated to an enzymatic marker such as alkaline phosphatase or horseradish peroxidase. Such enzymatic markers can be detected in standard colorimetric reactions using a substrate for the enzyme. Substrates for alkaline phosphatase include 5-bromo-4-chloro-3-indolylphosphate and nitro blue tetrazolium. Diaminobenzidine can be used as a substrate for horseradish peroxidase.

The probes and probe sets useful with the methods of the invention can be packaged with other reagents into kits to be used in carrying out the methods of the invention.

Preferred Probe Set.

A preferred probe composition is the LAVysion Multi-Color Probe Set (Abbott Molecular, Inc.). The LAVysion Multi-color Probe consists of a mixture of four directly labeled DNA FISH probes. The LSI EGFR Probe is labeled in SpectrumRed and covers an approximately 300 kb region that contains the entire EGFR gene (7p12). The Spectrum-Gold labeled LSI C-MYC Probe covers an approximately 750 kb region that contains the entire CMYC gene (8q24.12-q24.13). The LAVysion Multi-color Probe also contains the SpectrumGreen labeled LSI D5S23, D5S271 that covers an approximately 450 kb region at 5p15.2. The last component is the CEP 6 probe labeled in SpectrumAqua that hybridizes to the alpha satellite DNA region located at the centromere of chromosome 6 (6p11.1-q11). This probe set is available commercially premixed in a suitable hybridization buffer. The individual probes in the LAVysion Set are each available commercially as single ASR labeled probes from Abbott Molecular, Inc.

Preparation of Samples.

A biological sample is a sample that contains cells or cellular material, including cell-containing extracts from a patient sample. For example, lung samples are typically cells or cellular material derived from pulmonary structures, including but not limited to lung parenchyma, bronchioles, bronchial, bronchi, and trachea. Non-limiting examples of biological samples useful for the detection of lung cancer include bronchial specimens, resected lung tissue, lung biopsies, and sputum samples. Examples of bronchial specimens include bronchial secretions, washings, lavage, aspirations, and brushings. Lung biopsies can be obtained by methods including surgery, bronchoscopy, fine needle aspiration (FNA), and transthoracic needle biopsy. In one example, touch preparations can be made from lung biopsies. The inventive assays can also be performed on a circulating tumor cell sample derived from a blood sample from an early stage NSCLC patient. A circulating tumor cell sample can be prepared using the immunomagnetic separation technology available from Immunicon.

Tissues can be fixed with a fixative such as formaldehyde and then embedded in paraffin. Sections are then cut using a microtome and are applied to a microscope slide. Cytology specimens can be prepared from cellular suspensions derived from FNA, bronchial washings, bronchial lavage, or sputum, or disseminated tissue cells. Cytology specimens can be prepared by fixation of cells in ethanol or methanol:acetic acid combined with cytocentrifugation, thin layer deposition methods (e.g. ThinPrep, Cytyc Corp.), smears, or pipetting onto microscope slides. In addition, biological samples can include effusions, e.g., pleural effusions, pericardial effusions, or peritoneal effusions.

Hybridization Methods.

Any suitable in situ hybridization method can be used. Prior to in situ hybridization, chromosomal probes and chromosomal DNA contained within the cell each are denatured. If the chromosomal probes are prepared as a single-stranded nucleic acid, then denaturation of the probe is not required. Denaturation typically is performed by incubating in the presence of high pH, heat (e.g., temperatures from about 70.degree. C. to about 95.degree. C.), organic solvents such as formamide and tetraalkylammonium halides, or combinations thereof. For example, chromosomal DNA can be denatured by a combination of temperatures above 70.degree. C. (e.g., about 73.degree. C.) and a denaturation buffer containing 70% formamide and 2.X SSC (0.3M sodium chloride and 0.03 M sodium citrate). Denaturation conditions typically are established such that cell morphology is preserved. For example, chromosomal probes can be denatured by heat, e.g., by heating the probes to about 73.degree. C. for about five minutes.

After removal of denaturing chemicals or conditions, probes are annealed to the chromosomal DNA under hybridizing conditions. "Hybridizing conditions" are conditions that facilitate annealing between a probe and target chromosomal DNA. Hybridization conditions vary, depending on the concentrations, base compositions, complexities, and lengths of the probes, as well as salt concentrations, temperatures, and length of incubation. For example, in situ hybridizations are typically performed in hybridization buffer containing 1-2.X.SSC, 50-55% formamide, a hybridization acceleratant (e.g. 10% dextran sulfate), and unlabeled blocking DNA to suppress non-specific hybridization. In general, hybridization conditions, as described above, include temperatures of about 25 degree C. to about 55 degree C., and incubation lengths of about 0.5 hours to about 96 hours. More particularly, hybridization can be performed at about 32 degree C. to about 45 degree C. for about 2 to about 16 hours.

Non-specific binding of chromosomal probes to DNA outside of the target region can be removed by a series of washes with a salt solution. Temperature and concentration of salt in each wash depend on the desired stringency. For example, for high stringency conditions, washes can be carried out at about 65.degree. C. to about 80.degree. C., using 0.2.X to about 2.X.SSC, and about 0.1% to about 1% of a non-ionic detergent such as Nonidet P-40 (NP40). Stringency can be lowered by decreasing the temperature of the washes or by increasing the concentration of salt in the washes.

A preferred method using a four-color probe fluorescently labeled probe composition is described in the Example section below. The hybridization of the probes to the tissue sample can be performed manually, or with the assistance of instruments, such as the ThermoBrite hybridization oven, the VP 2000 Processor, or the XMatrix™ processing instrument (all available commercially from Abbott Molecular, Inc.).

Pre-Selection of Cells.

Cell samples can be evaluated preliminarily by a variety of methods and using a variety of criteria. The probes and methods described herein are not limited to usage with a particular screening methodology. One example is the "scanning method" wherein the observer scans hundreds to thousands of cells for cytologic abnormalities, e.g., as viewed with a DAPI filter. The number of cells assessed will depend on the cellularity of the specimen, which varies from patient to patient. Cytologic abnormalities commonly but not invariably associated with dysplastic and neoplastic cells include nuclear enlargement, nuclear irregularity, and abnormal DAPI staining (frequently mottled and lighter in color). In the scanning step, the observer preferably focuses the evaluation of the cells for chromosomal abnormalities (as demonstrated by FISH) to those cells that also exhibit cytological abnormalities. In addition, a proportion of the cells that do not have obvious cytologic abnormalities can be evaluated since chromosomal abnormalities also occur in the absence of cytologic abnormalities. This scanning method is described in further detail in U.S. Pat. No. 6,174,681 to Halling, et al., which is incorporated herein by reference. Lung cancer cells can be selected for evaluation using the method described in US Patent Pub. 2003/0087248 A1 by Morrison, et al., which is incorporated herein by reference.

Regions of the specimen may also be selected for evaluation using conventional stains, such as stains containing hematoxylin and eosin. For example, a pathologist can stain a section of a paraffin-embedded specimen with a hematoxylin/eosin stain, identify a region as probably cancerous by tissue morphology and staining pattern, and outline that region with a felt tip ink pen or glass scribe. The marked region is then transferred to the corresponding location on a serial section of the paraffin-embedded specimen with a glass scribe, and FISH is performed on that slide. Cells within the scribed region are then evaluated for FISH signals.

Detection of Classification Patterns of Chromosomal Abnormality.

Abnormal cells are characterized by the presence of one or more patterns of chromosomal copy number abnormalities. The presence of a copy number abnormality pattern in a cell in the patient sample is assessed by examining the hybridization pattern of the chromosomal probe (e.g., the number of signals for each probe) in the cell, and recording the number of signals. Aneusomy is typically intended to mean abnormal copy number, either of the whole chromosome or a locus on a chromosome. Abnormal copy number includes both monosomy (one copy) and nullsomy (zero copies) of the autosomes, also referred to as a deletion, and greater than 2 copies, which for a particular chromosomal locus is sometimes referred to as gene amplification (alternatively, amplification is reserved for the situation in which the gene copy number exceeds the copy number of the chromosome in which it is contained). However, sectioning of paraffin-embedded specimens (typically 4-6 μm) may result in truncation of cell nuclei such that the number of FISH signals per cell for some cells will be somewhat lower than the actual number of copies in an intact nucleus. In the five classifiers of the invention, the absolute number of particular FISH probe hybridization signals for each probe is determined and then used in various ratio comparisons.

Test samples can comprise any number of cells that is sufficient for a clinical diagnosis, and in a preferred paraffin-embedded tissue sample, the hybridization pattern is typically assessed in about 20 to about 200 cells. It is preferred to assess the hybridization pattern in about 40 to about 120 cells per sample.

Figure 1:
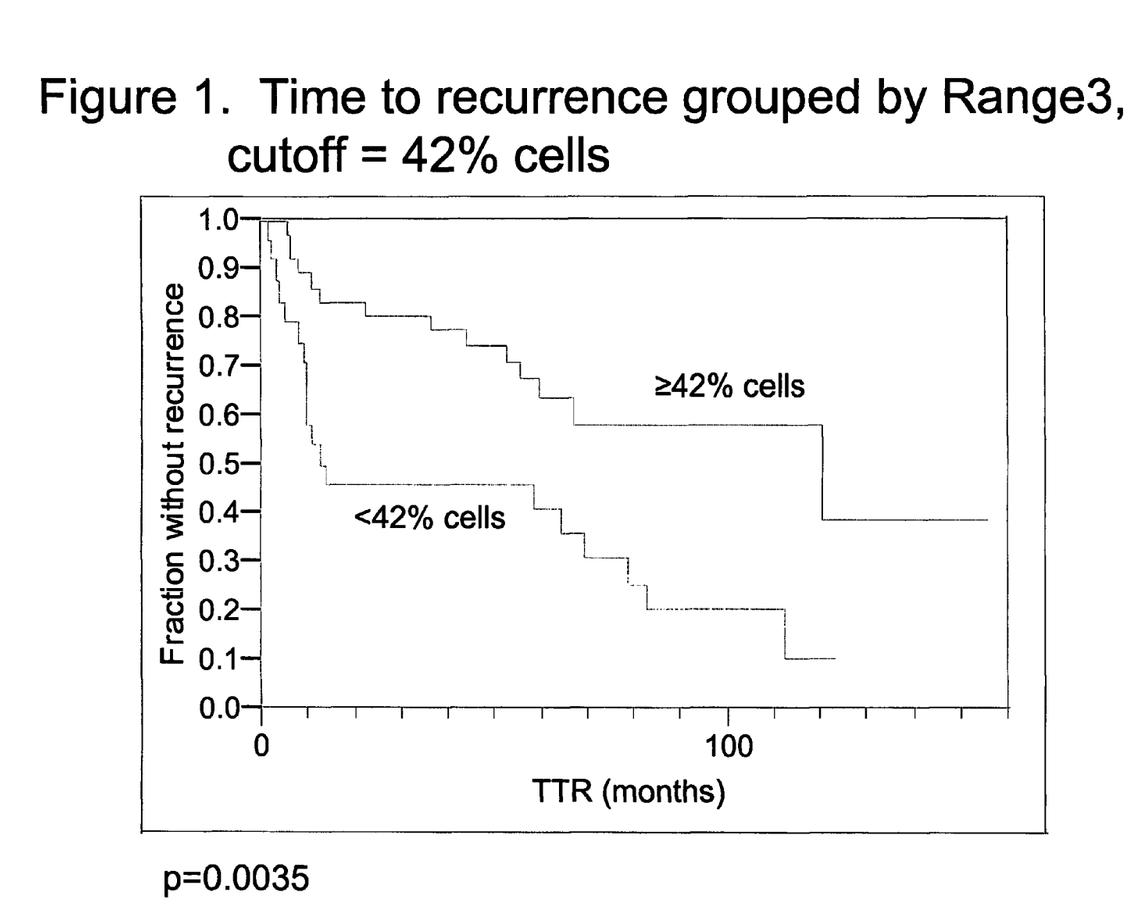
FIG. 1 is a Kaplan-Meyer curve showing the time to lung cancer recurrence for a 60 patient cohort with early stage NSCLC, classified by the Range3 pattern.

The Range3 classifier determined the percentage of cells containing a range of FISH signals >3 (i.e. locus with largest number of FISH signals minus locus with lowest number of FISH signals on a cell-by-cell basis). The Range3 classifier did not rely on any particular FISH signal, but was a comparison in each cell of the highest to lowest number of signals. Range3, using a cutoff of 42% cells showing on a cell by cell basis a difference of more than 3 signals between the probe with the highest number of hybridization signals and the probe with the lowest number of hybridization signals, was capable of dividing patients into a group of 36 (≥42% cells) in which 29 of these patients (80.6%) had the favorable prognosis, and a group of 24 (<42% cells) in which only 11 (45.8%) had the favorable prognosis (p=0.011). Median times to progression in the former and latter groups were 121 and 14.5 months, respectively (p=0.0035). FIG. 1 is a Kaplan-Meyer plot of the time to lung cancer recurrence for the favorable and unfavorable patient prognostic groups identified by the Range3 classifier.

Figure 2:
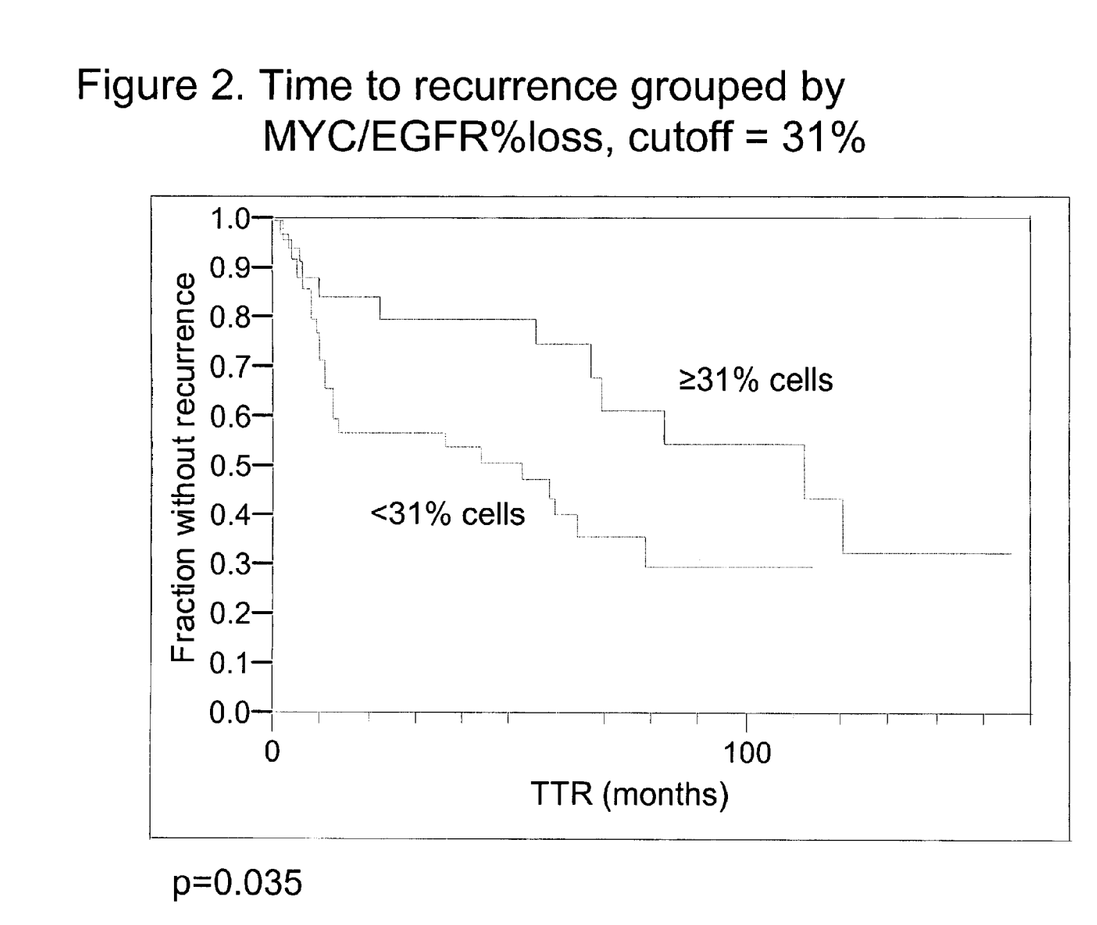
FIG. 2 is a curve showing the time to lung cancer recurrence for a 60 patient cohort with early stage NSCLC, classified by the MYC/EGFR % loss pattern.

The MYC/EGFR % loss pattern classifier looks to the ratio of the number of cells showing a relative loss of MYC probe signals to those from the EGFR probe. The MYC/EGFR % loss was the percentage of cells that showed fewer MYC signals than EGFR signals. The MYC/EGFR % loss classifier, using a cutoff of 31% cells, was capable of dividing patients into a group of 25 (~31% cells) in which 20 (80.0%) had the favorable prognosis, and a group of 35 in which 20 (57.1%) had the favorable prognosis (p=0.096). Median times to progression in the former and latter groups were 113 and 53.3 months, respectively (p=0.0346). FIG. 2 is a Kaplan-Meyer plot of the time to lung cancer recurrence for the favorable and unfavorable patient prognostic groups identified by the MYC/EGFR % loss classifier.

Figure 3:
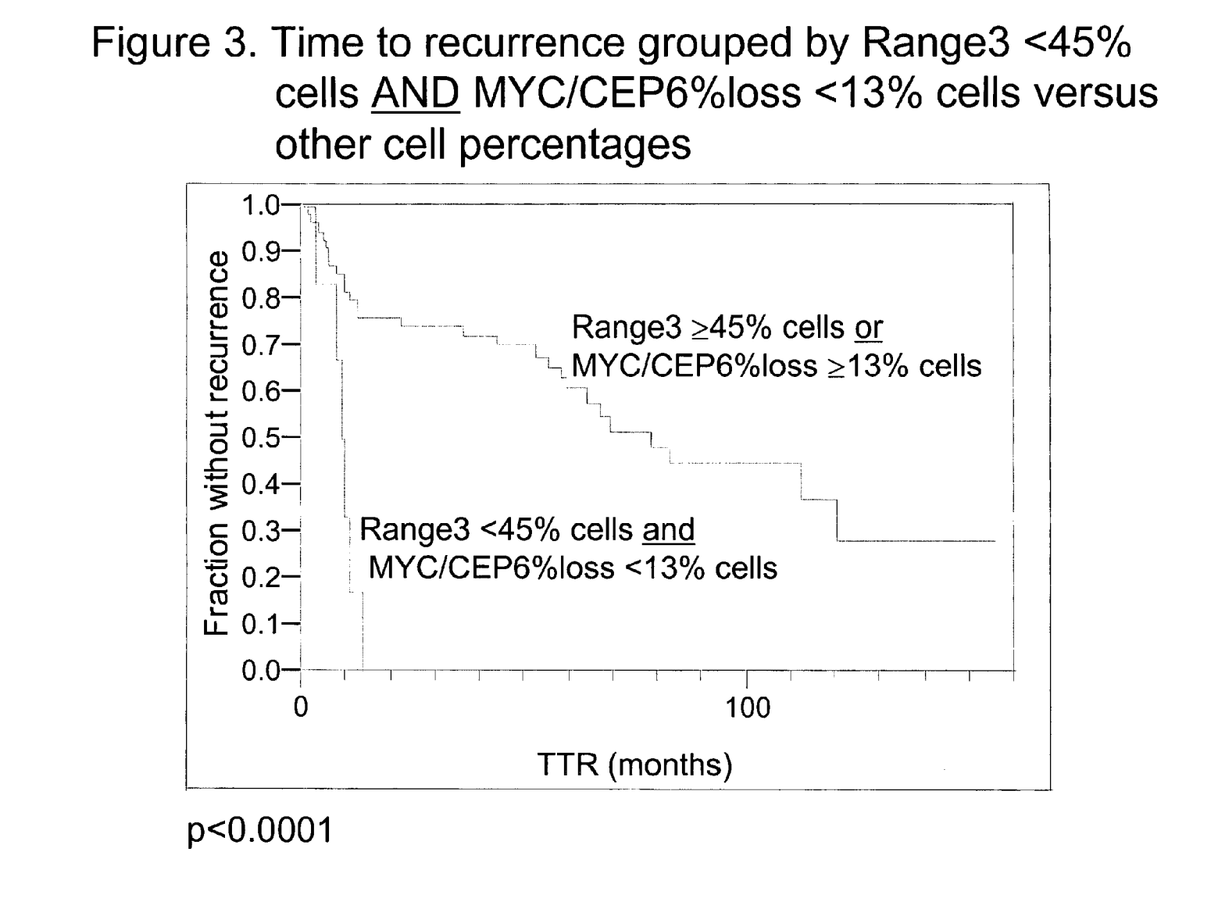
FIG. 3 is a Kaplan-Meyer curve showing the time to lung cancer recurrence for a 60 patient cohort with early stage NSCLC, classified by the combination of the Range3 pattern and the MYC/CEP6 ratio pattern.
Figure 4:
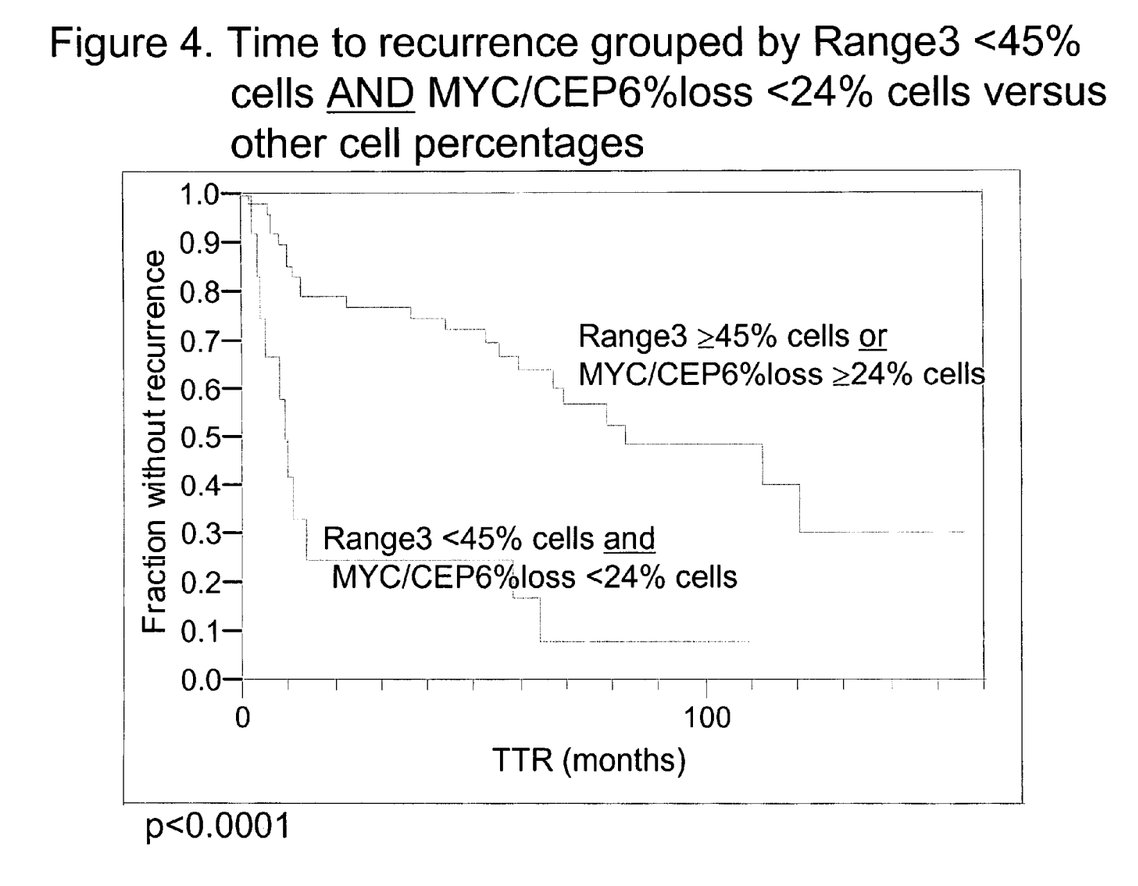
FIG. 4 is a Kaplan-Meyer curve showing the time to lung cancer recurrence for a 60 patient cohort with early stage NSCLC, classified by the combination of the Range3 pattern and the MYC/CEP6 ratio pattern, but with a higher cutoff of the percent cells having the MYC/CEP6 pattern.

The combination of the Range3 pattern with the MYC/CEP6% loss pattern was assessed. The MYC/CEP6% loss was the percentage of cells that showed fewer MYC signals than CEP6 signals. Where the Range3 pattern is present in <45% of the cells and the MYC/CEP6% loss pattern is present in <13% of the cells, then a group of 6 (10% of the cohort) patients is identified in which all six had unfavorable prognosis (all progressing within 15 months). Of the remaining 54 patients (in which the Range3 pattern was in ≥45% cells or the MYC/CEP6% loss was present in ≥13% cells), 40 (74.1%) had the favorable prognosis (p=0.0008). Median times to disease recurrence in the former and latter groups were 10.1 and 78.8 months, respectively (p<0.0001). FIG. 3 is a Kaplan-Meyer plot of the time to lung cancer recurrence for the favorable and unfavorable patient prognostic groups identified by the combination of Range3 and MYC/CEP6% loss classifier. FIG. 4 is a Kaplan-Meyer plot of the time to lung cancer recurrence for the favorable and unfavorable patient prognostic groups identified by the combination of Range3 and MYC/CEP6% loss classifier, but using a higher percent cutoff of cells with the MYC/CEP6% loss pattern.

Figure 5:
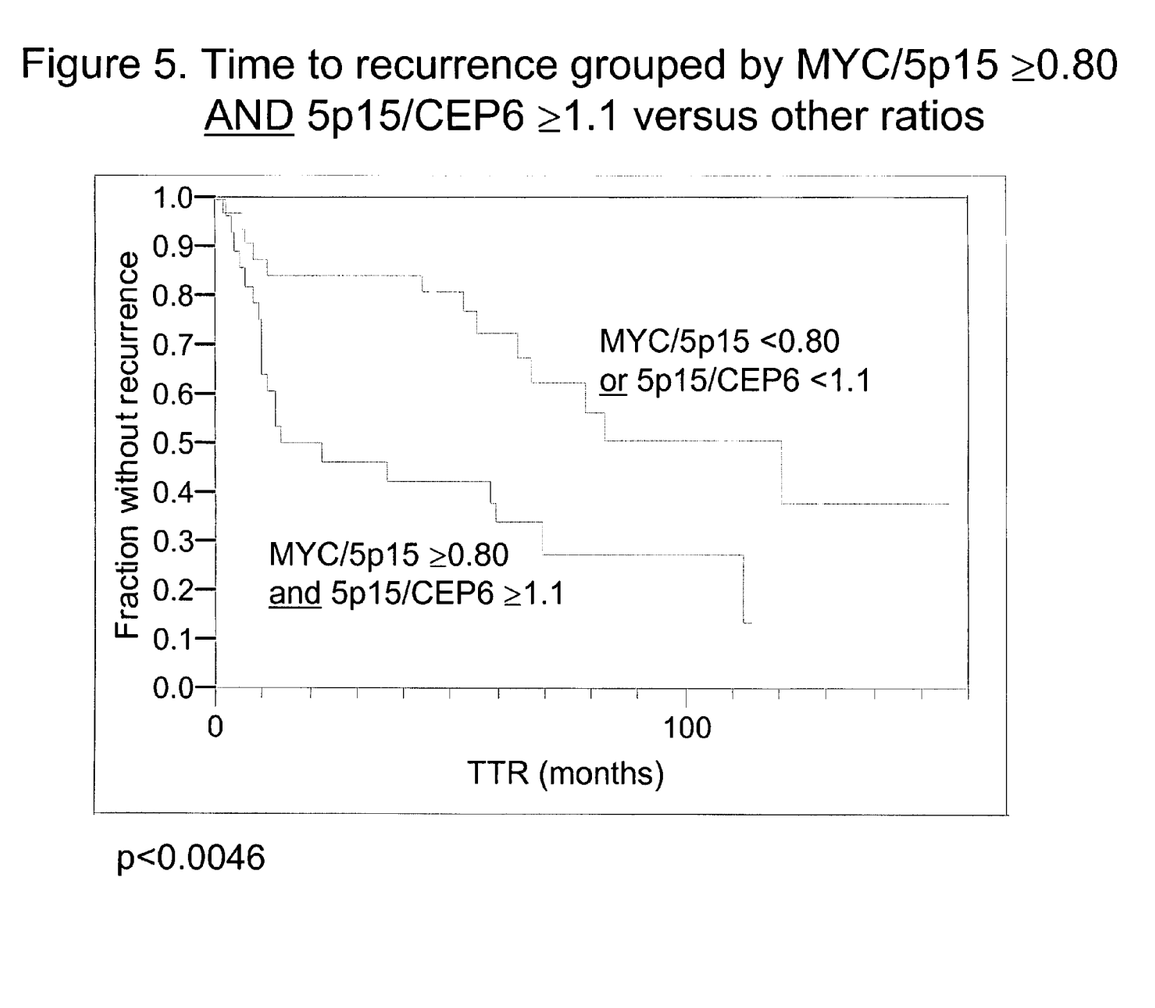
FIG. 5 is a Kaplan-Meyer curve showing the time to lung cancer recurrence for a 60 patient cohort with early stage NSCLC, classified by the combination of the MYC/5p15 ratio pattern and the 5p15/CEP6 ratio pattern.

The combination of the MYC/5p15 overall signal ratio >0.8 and the 5p15/CEP6 overall ratio >1.1 also provided statistically significant prognostic classification. The overall ratios are obtain by summing the signals for the MYC probe across all cells enumerated in the specimen, and dividing by the sum of the signals for the 5p15 probe across all cells enumerated in the specimen. This combination classifier identified a group of 28 patients in which 13 (46.4%) had the favorable prognosis. Of the remaining 32 patients (those with the MYC/5p15 signal ratio less than 0.80 or those with the 5p15/CEP6 signal ratio <1.1), 27 (84.4%) had the favorable prognosis (p=0.0026). Median times to progression in the former and latter groups were 22.7 and 121 months, respectively (p=0.0046). FIG. 5 is a Kaplan-Meyer plot of the time to lung cancer recurrence for the favorable and unfavorable patient prognostic groups identified by the combination classifier of MYC/5p15 and the 5p15/CEP6.

The combination of the Average Signal Range ≥2.5 with the Range3 pattern present in less than 42% of the assessed cells also provides a significant prognostic classification. In this combination classifier, the Average Signal Range is calculated using the total number of cells in the tissue sample that are assessed, by determining in each cell the difference between the probe with the highest number of hybridization signals and the probe with the lowest number of probe signals, independent of the target locus of the particular probe that has the highest or lowest number of signals, and then summing up the individual cell Signal Range number and dividing by the number of cells assessed to produce the Average Signal Range number. A cutoff in the Average Signal Range of greater than or equal to 2.5 produced the best prognostic classification in combination with the Range3 signal pattern in less than 42% of the cells. This combination classifier identified a group of 12 patients in which 2 (16.7%) had the favorable prognosis. Of the remaining 48 patients (those with the Average Signal Range <2.5 and the Range3 pattern in ≥42% of cells), 38 (79.2%) had the favorable prognosis (p=0.0001). Median times to progression in the former and latter groups were 9.86 and 83.1 months, respectively (p<0001).

Details of the invention are further described in the following examples, which are not intended to limit the scope of the invention as claimed. One of skill in the art will recognize that variations and modifications of the invention may be apparent upon reviewing the instant specification. It is therefore an object to provide for such modifications and variations of the embodiments described herein, without departing from the scope or the spirit of the invention.

EXAMPLES

Experimental Methods
Specimens.
Tissue specimens from 60 NSCLC patients were obtained from the archives of the Pathology Department of Rush University Medical Center (Chicago, Ill.). All patients had been diagnosed as Stage 1b or Stage II, and were treated with surgical resection without any follow-up or neoadjuvant chemotherapy. Chart review and study analyses were approved by the RUMC Institutional Review Board. The diagnosis of early stage NSCLC in the archival material was obtained from pathology reports. Times to recurrence of lung cancer were obtained from the patient charts. Of the 60 patients, 16 had recurrent lung cancer within one year, four had recurrent lung cancer between one and three years, 16 had recurrent lung cancer after 3 years and 24 never progressed (with 34.5 months minimum follow-up).

In Situ Hybridization.
For copy number analyses by FISH, the LAVysion probe set was hybridized to the patient specimen. Specimen slides were prepared using either the Vysis Paraffin Pretreatment II or III kits (Abbott Molecular Inc.). The prepared specimen slides were hybridized with the four color probe solution in a HYBrite™ automated co-denaturation oven (Abbott Molecular Inc.). The slides were placed on the oven surface and 10 µL probe solution was layered over the tissue section. A cover slip was applied over the probe solution and sealed to the slide with rubber cement. After denaturation at 73° C. for 5 minutes, the probe was hybridized at 37° C. for 16-18 hr. Following hybridization and removal of the rubber cement seal, the slides were placed in room-temperature 2×SSC (SSC=0.3 M NaCl, 15 mM sodium citrate), 0.3% Nonidet P40 (NP40) for 2-5 min to detach the cover slips. The slides were then immersed in 73° C. 2×SSC, 0.3% NP40 for 2 min to remove nonspecifically bound probe and then were allowed to dry in the dark. DAPI I antifade solution (Abbott Molecular Inc.) was applied to the specimen for visualization of the nuclei. Some of the specimens required additional processing to yield optimal FISH results.

The FISH slides were evaluated under a Zeiss Axioscope epi-fluorescence microscope (Carl Zeiss, Thornwood, N.Y.). Signals were visualized and counting performed with a DAPI single-band-pass filter set to visualize nuclei, a gold single-band-pass filter set to visualize the SpectrumGold-labeled 8q24 probe, a blue single-band-pass filter set to visualize the SpectrumAqua-labeled CEP6 probe, a red single-band-pass filter set to visualize the SpectrumRed-labeled 7p12 probe and a green single-band-pass filter set to visualize the SpectrumGreen-labeled 5p15 probe (all filter sets from Abbott Molecular Inc.). Only nuclei with morphology characteristic of malignant cells were counted. When a slide was counted multiple times, counts were combined and used for recalculating the hybridization signal ratios and signal patterns. FISH signals were enumerated in 40 to 120 cells (mean=82 cells) per specimen to obtain copy numbers for each of the four loci.

A range of cutoff points were analyzed by first generating cutoffs from the mean minus 2 standard deviations to the mean plus 2 standard deviations, in 0.1 standard deviation increments, for each parameter (ratios and % gains), using the mean and standard deviations of the patients with the favorable prognosis (patients that did not recur or recurred after 3 years). Each ratio and % signal gains or loss at each cutoff were compared with time to disease recurrence (greater than or less than 3 years to recurrence) in contingency tables. Cutoffs with the lowest chi-square probabilities were selected for further analysis.

Statistical Methods.
Association between selected classifiers and outcomes was performed using the Fisher's Exact Test. The level of significance wasp<0.05 in two-tailed estimates. The Kaplan-Meier method was used to determine median time to recurrence, with comparison between groups assessed by log-rank test (p<0.05 significance).

Results

Several classifications were found to associate strongly with prognosis when patients that progressed within 3 years of surgery (the unfavorable prognosis group) were compared to patients that either did not progress or progressed more than 3 years post surgery (the favorable prognosis group), or when median times to progression (nR) times were compared between patient groups distinguished by the classifiers.

Range3 Classifier.

This classifier determined the percentage of cells containing a range of FISH signals >3 (i.e. locus with largest number of FISH signals minus locus with lowest number of FISH signals on a cell-by-cell basis). Range3, using a cutoff of 42% cells, was capable of dividing patients into a group of 36 (≥42% cells with signal difference >3) in which 29 (80.6%) had the favorable prognosis, and a group of 24 (<42% cells with signal difference >3) in which only 11 (45.8%) had the favorable prognosis (p=0.011). Median times to progression in the former and latter groups were 121 and 14.5 months, respectively (p=0.0035). Table 1 shows the data for this classifier. FIG. 1 shows a Kaplan-Meyer plot of time to recurrence (TTR) in the two groups.

TABLE 1

Outcome grouped by Range3, cutoff = 42% cells

| FISH status | No progression or progression after 3 yr | Progression less than 3 yr | Total patients |
| --- | --- | --- | --- |
| ≥42% cells | 29 pts<br>80.6% | 7 pts<br>19.4% | 36 pts |
| <42% cells | 11 pts<br>45.8% | 13 pts<br>54.2% | 24 pts |
| Total patients | 40 pts | 20 pts | 60 pts | p = 0.011

MYC/EGFR % Loss Classifier.

The percentage of cells containing fewer MYC signals than EGFR signals, the MYC/EGFR % loss, using a cutoff of 31% of cells having a relative loss of MYC signals, was capable of dividing patients into a group of 25 (≥31% cells with a relative MYC loss) in which 20 (80.0%) had the favorable prognosis, and a group of 35 (<31% cells with a relative MYC loss) in which 20 (57.1%) had the favorable prognosis (p=0.096). Median times to progression in the former and latter groups were 113 and 53.3 months, respectively (p=0.0346). FIG. 2 shows a Kaplan-Meyer plot of time to recurrence (TTR) in the two groups. Table 2 shows the data for this classifier.

TABLE 2

Outcome grouped by MYC/EGFR%loss, cutoff = 31%

| FISH status | No progression or progression after 3 yr | Progression less than 3 yr | Total patients |
| --- | --- | --- | --- |
| ≥31% cells | 20 pts<br>80.00% | 5 pts<br>20.00% | 25 pts |
| <31% cells | 20 pts<br>57.14% | 15 pts<br>42.86% | 35 pts |
| Total patients | 40 pts | 20 pts | 60 pts | p = 0.096

Combination Classifier of Range3 and MYC/CEP6% Loss.

If the Range3 pattern is present in <45% cells and the MYC/CEP6% loss is present in <13% cells, then a group of 6 (10%) patients is identified in which all six had unfavorable prognosis (all patients recurred within 15 months). Of the remaining 54 patients (Range3 is present in ≥45% cells or MYC/CEP6% loss is present in ≥13% cells), 40 (74.1%) had the favorable prognosis (p=0.0008). Median times to progression in the former and latter groups were 10.1 and 78.8 months, respectively (p<0.0001). Table 3 shows the data for the combination classifier results using a MYC/CEP6% loss cutoff of 13% of cells. FIG. 3 shows a Kaplan-Meyer plot of time to recurrence (TTR) in the two groups with the 13% cutoff

TABLE 3

Outcome grouped by Range3 <45% cells and MYC/CEP6%loss <13% cells versus other cell percentages

| FISH status | No progression or progression after 3 yr | Progression less than 3 yr | Total patients |
| --- | --- | --- | --- |
| Range3 ≥45% cells or MYC/CEP6%loss ≥13% cells | 40 pts<br>74.07% | 14 pts<br>25.93% | 54 pts |
| Range3 <45% cells and MYC/CEP6%loss <13% cells | 0 pts<br>0.00% | 6 pts<br>100.00% | 6 pts |
| Total patients | 40 pts | 20 pts | 60 pts | p = 0.0008

For comparison purposes, a Kaplan-Meyer plot of time to recurrence (TTR) in the two groups using the combination classifier, but with a higher cutoff of 24% for the percentage of cells with MYC/CEP6% loss was also determined. Table 4 and FIG. 4 shows the data and the Kaplan-Meyer plot for the combination classifier with the higher cutoff. Although not as dramatic separation of prognosis is achieved, higher cutoffs for MYC/CEP6% loss also provide very low p-values (p=0.0013 for prognosis, p<0.0001 for median time to recurrence).

TABLE 4

Outcome grouped by Range3 <45% cells AND MYC/CEP6%loss <24% cells versus other cell percentages

| FISH status | No progression or progression after 3 yr | Progression less than 3 yr | Total patients |
| --- | --- | --- | --- |
| Range3 ≥45% cells or MYC/CEP6%loss ≥13% cells | 37 pts<br>77.08% | 11 pts<br>22.92% | 48 pts |
| Range3 <45% cells and MYC/CEP6%loss <13% cells | 3 pts<br>25.00% | 9 pts<br>75.00% | 12 pts |
| Total patients | 40 pts | 20 pts | 60 pts | p = 0.0013

Combination Classifier of MYC/5p15 and 5p15/CEP6.

Using a combination of the MYC/5p15 signal ratio is ≥0.80 and the 5p15/CEP6 ratio is ≥1.1 of the cells, identifies a group of 28 patients in which 13 (46.4%) had the favorable prognosis. Of the remaining 32 patients (those with MYC/5p15 signal ratio <0.80 or those with 5p15/CEP6 signal ratio <1.1), 27 (84.4%) had the favorable prognosis (p=0.0026). Median times to progression in the former and latter groups were 22.7 and 121 months, respectively (p=0.0046). Table 5 shows the data for the combination classifier results and FIG. 5 shows a Kaplan-Meyer plot of time to recurrence (TTR) in the two groups.

TABLE 5

Outcome grouped by MYC/5p15 ≥0.80 and 5p15/CEP6 ≥1 versus other ratios

| FISH status | No progression or progression after 3 yr | Progression less than 3 yr | Total patients |
| --- | --- | --- | --- |
| MYC/5p15 ≥0.80 and 5p15/CEP6 ≥1.1 | 13 pts<br>46.43% | 15 pts<br>53.57% | 28 pts |
| MYC/5p15 <0.80 or 5p15/CEP6 <1.1 | 27 pts<br>84.38% | 5 pts<br>15.63% | 32 pts |
| Total patients | 40 pts | 20 pts | 60 pts | p = 0.0026

Combination Classifier of Average Signal Range and Range3 Pattern.

Figure 6:
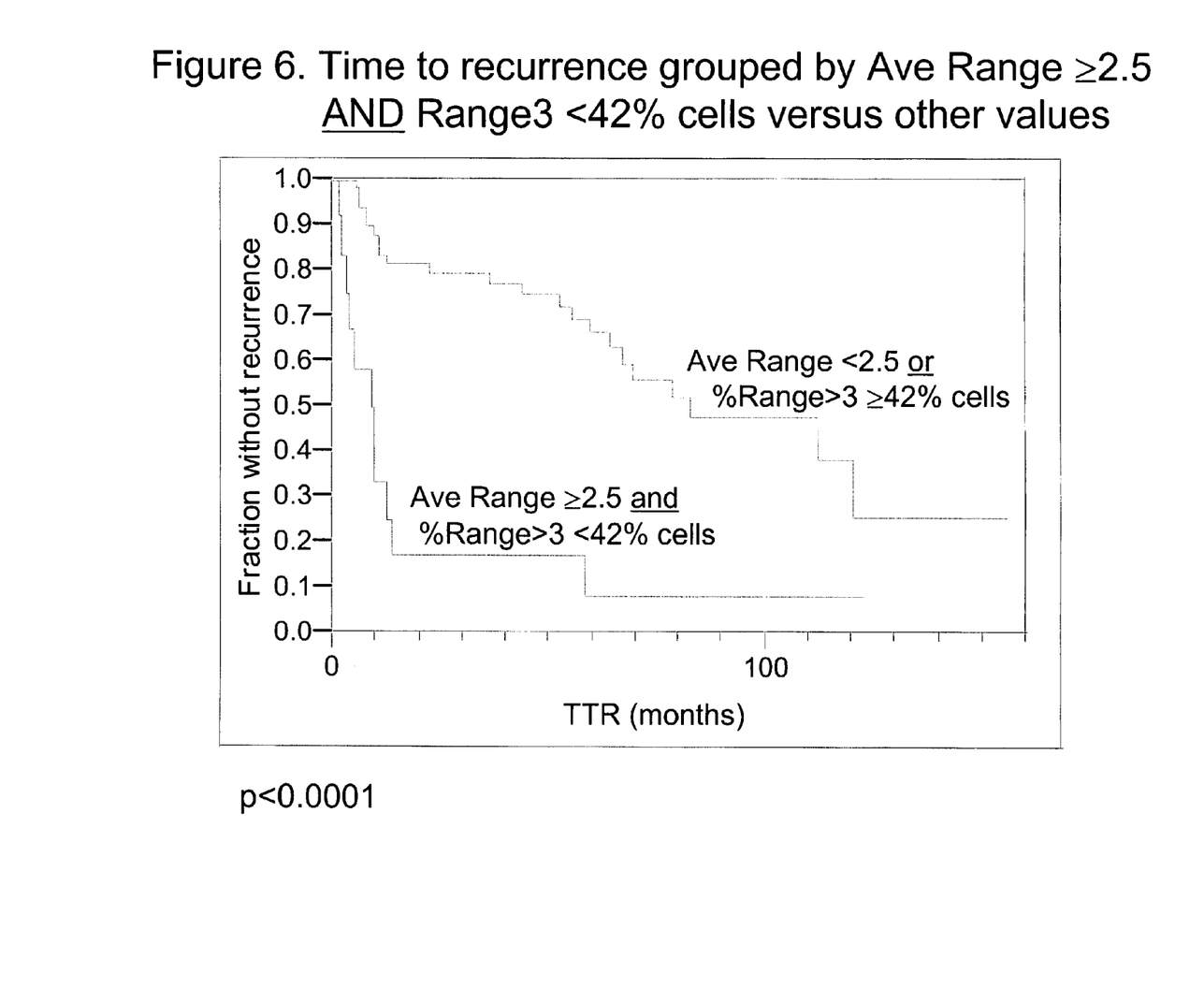
FIG. 6 is a Kaplan-Meyer curve showing the time to lung cancer recurrence for a 60 patient cohort with early stage NSCLC, classified by the combination of the average range of probe signal differences and the Range3 pattern.

This combination classifier (average Signal Range less than 2.5 or the Range3 pattern in at least 42% of cells) identified a group of 48 patients in which 38 (79.2%) had the favorable prognosis and 10 (20.8%) had the unfavorable prognosis. Of the remaining 12 patients (those with the Average Signal Range greater than or equal to 2.5 and the Range3 pattern in less than 42% of cells), only 2 (16.7%) had the favorable prognosis (p=0.0001), while 10 (83.3%) had the unfavorable prognosis. Median times to progression in the former and latter groups were 83.1 and 9.86 months, respectively (p<0.0001). Table 6 shows the data for the combination classifier results using a Range3 cutoff of less than 42% of cells. FIG. 6 shows a Kaplan-Meyer plot of time to recurrence (TTR) in the two groups.

TABLE 6

Outcome grouped by Ave Range ≥2.5 and Range3 <42% cells

| FISH status | No progression or progression after 3 yr | Progression less than 3 yr | Total patients |
| --- | --- | --- | --- |
| Ave Range ≥2.5 and Range3 <42% cells | 2 pts<br>16.67% | 10 pts<br>83.33% | 12 pts |
| Ave Range <2.5 or Range3 42% cells | 38 pts<br>79.17% | 10 pts<br>20.83% | 48 pts |
| Total patients | 40 pts | 20 pts | 60 pts | p = 0.0001

Discussion of Results

These data indicate that use of genomic copy number assessment of at least two of the EGFR, MYC, 5p15, and 6 loci measured by FISH, and with use of an appropriate classifier, is of prognostic importance in early stage NSCLC. All five of the classifiers tested were able to produce statistically significant classification of patients who had been treated with surgery without neoadjuvant or follow-up chemotherapy into favorable and unfavorable recurrence categories. No present clinical in vitro diagnostic assay provides this capability. This data is the first to classify early stage NSCLC patients with no distant metastasis or with spread to no more than one lymph node into favorable and unfavorable prognostic groups on a statistically significant basis using a molecular hybridization assay. FISH assays to two or more of the chromosomal loci 5p15, 7p12, 8q24 and centromere 6 performed on early stage NSCLC biopsy specimens or resected tumors appear valuable in decisions related to surgery and adjuvant therapy.

The associations in each of the classifiers were also fairly robust, in that statistical significance could be found over a range of cutoffs values as wide as 10% or more for some parameters. The cutoffs presented in the data for each classifier are the ones that had the lowest p-values. This means that the cutoff of the particular percentage of cells in the assessed tissue having the abnormal pattern or the cutoff of the particular ratio used in the classifier may be varied from that of the cutoff.

It is to be understood that, while the invention has been described in conjunction with the detailed description, thereof, the foregoing description is intended to illustrate and not limit the scope of the invention. Other aspects, advantages, and modifications of the invention are within the scope of the claims set forth below.

What is claimed is:

1. A method of treating early stage non-small cell lung cancer in a human patient, the method comprising:
    (a) obtaining a biological sample comprising a plurality of lung cancer cells from a human patient having early stage non-small cell lung cancer;
    (b) contacting the biological sample with a chromosome 8q24 locus specific probe and a chromosome 7p12 locus specific probe under conditions sufficient to enable hybridization of the probes to chromosomes in the lung cancer cells of the sample, wherein each of the chromosomal probes is directly labeled with a fluorescent label that can be separately detected;
    (c) performing fluorescence in situ hybridization (FISH) on the biological sample;
    (d) detecting less than 31% of lung cancer cells in the biological sample showing fewer 8q24 FISH probe signals than 7p12 FISH probe signals (8q24/7p12% loss pattern), which indicates a decreased time to recurrence (TTR) of lung cancer after surgical resection;
    (e) performing surgical resection of the lung cancer in the patient; and
    (f) administering adjuvant chemotherapy post-surgery or administering neoadjuvant chemotherapy before surgery.

2. The method of claim 1, wherein the biological sample is a lung tissue biopsy or resection.

3. The method of claim 1, wherein the patient has Stage 1b non-small cell lung cancer.

4. The method of claim 1, wherein the patient has Stage 2 non-small cell lung cancer.

5. The method of claim 1, wherein the contacting step (b) is performed on an automated instrument.

6. The method of claim 1, wherein the biological sample is a cytology sample.

* * * * *